(12) United States Patent
Kamal et al.

(10) Patent No.: US 7,087,641 B2
(45) Date of Patent: Aug. 8, 2006

(54) 4β-1"-[(2"-SUBSTITUTED BENZOYL) ANILINO]PODOPHYLLOTOXIN ANALOGUES USEFUL AS ANTICANCER AGENTS

(75) Inventors: Ahmed Kamal, Andhra Pradesh (IN); Peram Surakattula Murali Mohan Reddy, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 285 days.

(21) Appl. No.: 10/381,027

(22) PCT Filed: Mar. 28, 2002

(86) PCT No.: PCT/IN02/00091

§ 371 (c)(1),
(2), (4) Date: Sep. 9, 2003

(87) PCT Pub. No.: WO03/082876

PCT Pub. Date: Oct. 9, 2003

(65) Prior Publication Data

US 2005/0101804 A1    May 12, 2005

(51) Int. Cl.
*A61K 3/335*    (2006.01)
*A61K 31/34*    (2006.01)
*C07D 307/77*    (2006.01)

(52) U.S. Cl. .................. 514/463; 514/468; 549/298
(58) Field of Classification Search ............... 514/463, 514/468; 549/298
See application file for complete search history.

(56) References Cited

U.S. PATENT DOCUMENTS

| 5,300,500 | A  | * | 4/1994 | Lee et al. ............... 514/232.5 |
| 5,332,811 | A  |   | 7/1994 | Kuo-Hsiung et al. |
| 6,566,393 | B1 | * | 5/2003 | Lee et al. .................... 514/463 |
| 6,713,454 | B1 | * | 3/2004 | Ekwuribe et al. ............. 514/25 |
| 6,872,841 | B1 | * | 3/2005 | Lee et al. .................... 549/432 |
| 6,878,746 | B1 | * | 4/2005 | Monneret et al. ........... 514/468 |

OTHER PUBLICATIONS

Cho et al., "Antitumor Agents 163 Three-Dimensional Quantitative Structure-Activity Relationship Study of 4'-0-Demethylepipodopyllotoxin Analogs Using the CoMFA/q2-GRS Approach," Journal of Medicinal Chemistry, vol. 39, No. 7, 1996, pp. 1383-1395, XP-002222563.

* cited by examiner

*Primary Examiner*—Deborah C. Lambkin
(74) *Attorney, Agent, or Firm*—Foley & Lardner LLP

(57) ABSTRACT

The present invention provides a new class of compounds 4β-1"-[{2"-benzoyl substituted}anilino] podophyllotoxin exhibiting anti cancer activity and a process for preparing the same.

21 Claims, 3 Drawing Sheets

Podophyllotoxin

R= CH₃  Etoposide

R= [thiophene]  Teniposide

Where R is H or CH$_3$ and R$_1$=H, halogen, R$_2$=H, halogen, NO$_2$.

4β-1"-[(2"-SUBSTITUTED BENZOYL) ANILINO]PODOPHYLLOTOXIN ANALOGUES USEFUL AS ANTICANCER AGENTS

TECHNICAL FIELD

The present invention relates to a process for the synthesis of new 4β-1"-[2"-(substituted benzoyl)anilino]podophyllotoxin analogues are useful anticancer agents. The present invention particularly relates to the synthesis of new class of 4β-O-benzoyl anilino congeners of the podophyllotoxin as useful anticancer agents.

BACKGROUND ART

Etoposide and teniposide two synthetic podophyllotoxin derivatives which are important drugs that currently being used in the treatment of small lung cancer, testicular carcinoma, lymphoma, Kaposi's sarcoma. The clinical efficacy and intriguing mechanism of etoposide has greatly stimulated interest in further studies on the modification of the C-4 substution of this compound and for better antitumour activity (Jadine, I. In *Anticancer Agents Based on Natural Products Models;* Cassady, J. M., Dours, J., Eds.; Academic press: New York, 1980, p 319.; Levy, R. K.; Hall, I. H.; Lee, K. H. *J. Pharm. Sci.* 1983,72,1158.; Issell, B. F.; Muggia, F. M.; Carter, S. K. *Etoposide* [VP-16] *Current Status and New Developments;* Academic Press New York, 1984.; Stio, H.; Yoshikawa, H.; Nishimura, Y.; Kondo, S.; Takeuchi, T.; Umezawa, H. *Chem. Pharm. Bull.* 1986,34,3733. Satio, H.; Nishimura, Y.; Kondo, S.; Komuro, K.; Takeuchi, T.; *Bull. Chem. Soc. Jpn.*1988, 61, 2493). It has been well established that the principal mechanism of the action for etoposide is by the inhibition of catalytic activity of DNA topoisomarase II and concurrent enzyme mediated production of lethal DNA strand breaks. Structure activity relationship studies for the podophyllotoxin-derived compounds have shown the trans C/D ring juncture is a essential for the antitumour activity. A number of studies have been carried out on the structural modification of glycoside moiety by 4-alkylamino or 4-arylamino substituents have improved the inhibitory activity on human DNA topoisomarase II as well as stronger activity in causing cellular protein length DNA breakage (Lee. K. H.: Imakura. Y.: Haruna. M.; Beers, S. A.; Thurston, L. S.; Dai, H. J.; Chen, C. H.; Liu, S. Y.; Cheng, Y. C. *J. Nat. Prod.* 1989, 52, 606. Liu, S. Y.; Hawang, B. D.; Haruna, M.; Imakura, Y.; Lee, K. H.; Cheng, Y. C. *Mol. Pharmcol.* 1989, 36, 78. Lee, K, H.; Beers, S. A.; Mori, M.; Wang, Z. Q.; Kuo, Y. H.; Li, L.; Liu, S. Y.; cheng, Y. C.; *J. Med. Chem.* 1990, 33,1364). In the context a large number of 4β-aryl amino derivatives of 4'-O-demethyl epipodophyllotoxin based compound have been synthesized and investigated for their antitumour activity.

OBJECTIVES OF THE INVENTION

The main object of the invention is to provide the new 4β-[2"-benzoylsubstituted] arylamino podophyllotoxin analogues useful as anticancer agents.

Another object of the present invention is to provide a process for the synthesis of new 4β-1"-[{2"-benzoyl substituted}anilino] podophyllotoxin derivatives as useful anticancer agents, which obviates the draw backs as detailed above.

Another object of the present invention is to provide new and stereo-selective compounds of the podophyllotoxins and 4'-O-demethylepipodophyllotoxin in good yields.

Still another object of the present invention is to provide the key step for the synthesis of these analogues by direct nucleophilic substitution of the C-4β-bromo intermediate.

SUMMARY OF THE INVENTION

The above and other objective of the present invention are achieved by providing the new class of $C_4$-β-aryl substituted and N-linked derivatives of podophyllotoxin and 4'-O-demethylepipodophyllotoxin, which have been synthesized as anti cancer agents.

Accordingly, the present invention provides new class of 4β-1"-[{2"-benzoyl substituted}anilino] podophyllotoxin analogues having the structural formula (2).

The present invention also provides a process for the preparation of new 4β-1"-[2"-(substituted benzoyl)anilino] podophyllotoxin analogues as useful anticancer agents. More particularly, it provides a process for the preparation of 4β-1"-[2"-(substituted benzoyl)anilino] derivatives of podophyllotoxin.

BRIEF DESCRIPTION OF THE ACCOMPANYING DRAWINGS

Figure 1:
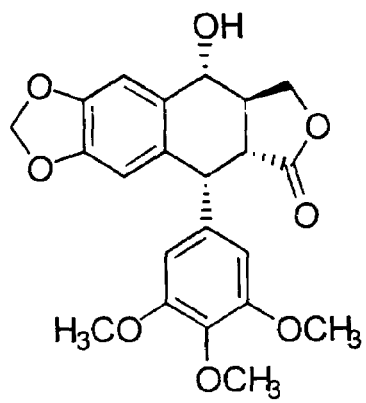
FIG. 1 represents structure of podophyllotoxin, Etoposide and Teniposide.
Figure 1:
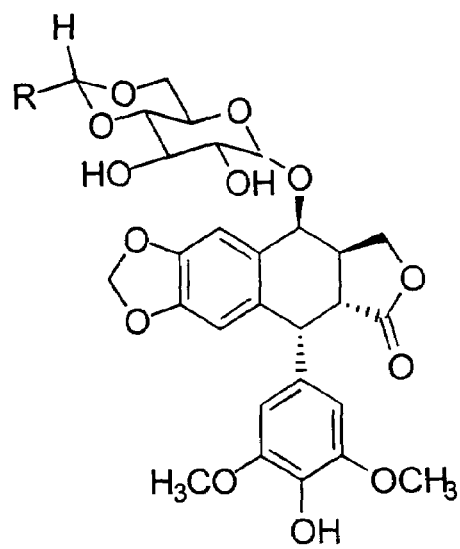
Figure 1:
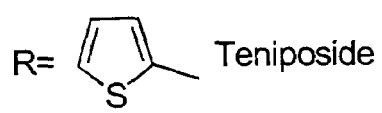
Figure 2:
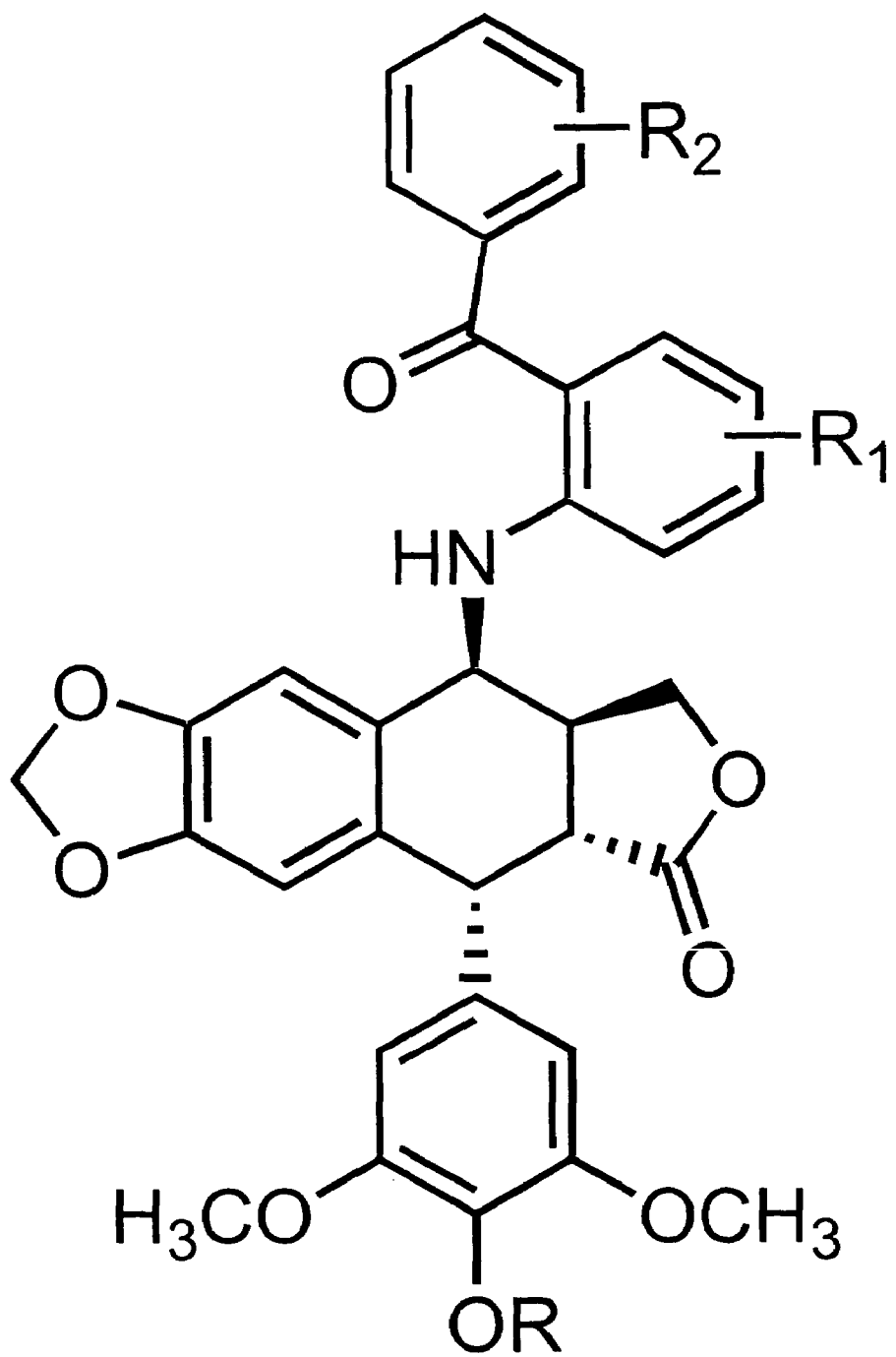
FIG. 2 represents general formula of compounds of the class 4β-1"-[{2"-benzoyl substituted}anilino] podophyllotoxin analogues.
Figure 3:
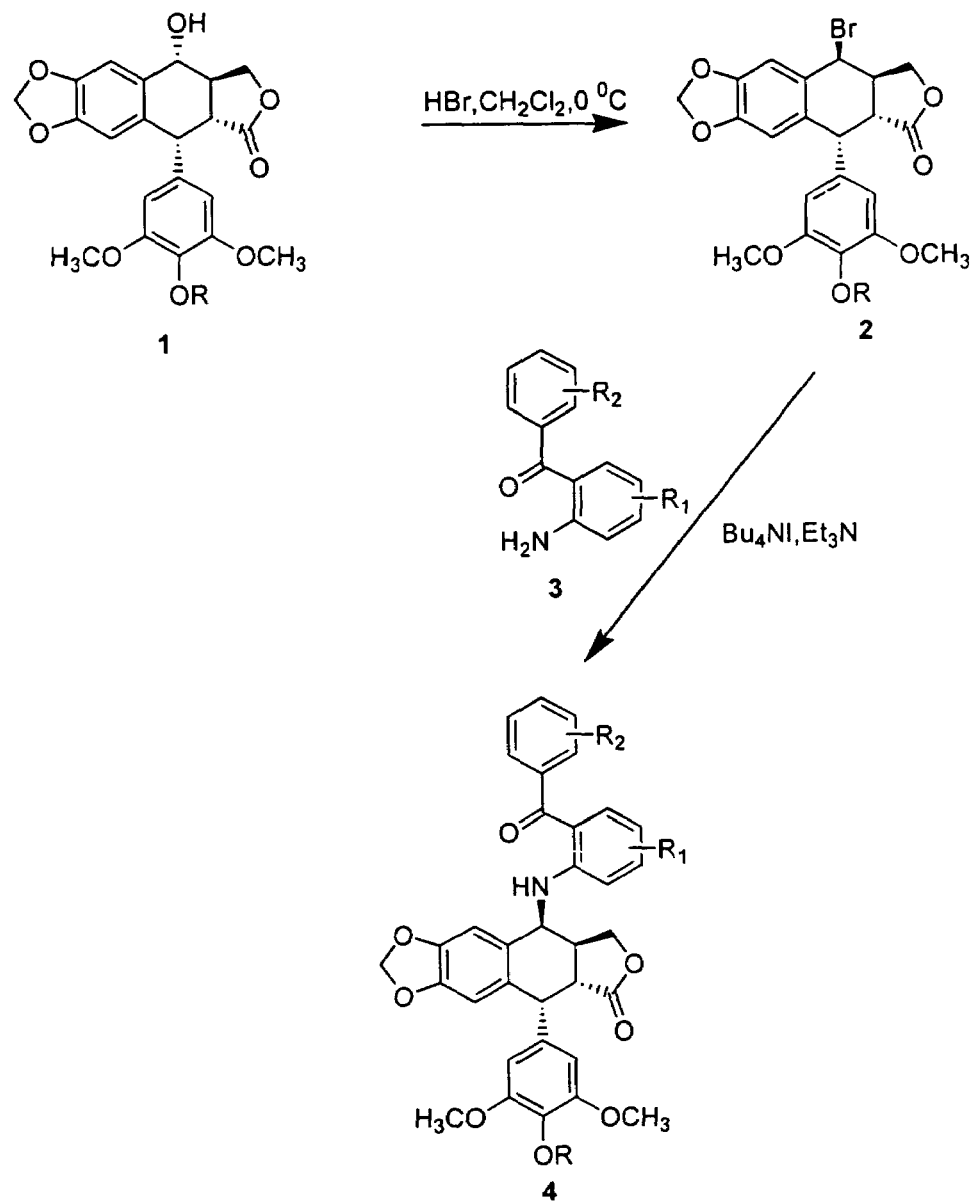

FIG. 3 discloses the process for the synthesis of new podophyllotoxin analogues as anticancer agents producing the novel and stereo-selective derivatives of the podophylotoxin in good yields.

DETAILED DESCRIPTION

The process for the synthesis of new podophyllotoxin analogues as anticancer agents produces the novel and stereo-selective derivatives of the podophyllotoxin in good yields, where in the key step for the synthesis of these analogues is by direct nucleophilic substitution of C-4β-bromo intermediates, 4β-bromo-podophyllotoxin and 4'-O-demethylepipodophyllotoxin, which have been reacted with substituted or unsubstituted 2-aminobenzophenones in a stereo-selective manner to afford the 4β-1"-[{2"-benzoyl substituted}anilino] podophyllotoxin derivatives.

These 4-bromopodophyllotoxin intermediates have been prepared by the bromination of the related podophyllotoxin compounds as described in the literature [Kuhn, M.; Keller-Juslen, C.; Van Wartburg, *Helv. Chemica. Acta,* 1969, 52, 944].

In an embodiment of the present invention, the naturally occurring podophyllotoxin lignan was isolated from *Podophyllum peltatum linnaeus.*

In another embodiment of the present invention the synthesis of 4β-intermediates have been carried out from bromination of podophyllotoxin and 4'-O-demethylepipodophyllotoxin.

In yet another embodiment of the present invention 1–2 eq. of different unsubstituted and substituted benzophenone compounds have been used.

In still another embodiment of the present invention a variety of solvents were used for the nucleophilic substitution step, such as dichloromethane, chloroform and tetrahydrofuran.

In still yet another embodiment of the present invention catalytic amount of $Bu_4N^+I^-$ (0.2–0.5eq) was used by stirring the reaction mixture between −10° C. to room temperature for 2 to 10 h.

In still another embodiment of the present invention bases like $K_2CO_3$, $Et_3N$ were also used.

In still another embodiment of the present invention the purification of these analogues was done by column chromatography employing chloroform/methanol as eluent.

Thus, the present invention provides new classes of podophyllotoxin analogues, which were synthesized in a stereo selective manner.

A program was initiated in the laboratory for the design and synthesis of new 4β-aryl amino substituted podophyllotoxin congeners with enhanced antitumour activity and/or activity against etoposide resistant tumor cell lines. In these efforts new 4β-1"-[{2"-benzoyl substituted}anilino] podophyllotoxin derivatives have been synthesized and evaluated for their cytotoxicity and anticancer potency. Interestingly, some of the compounds have shown greater in vitro cytotoxicity values compared to etoposide. The synthesis of these compounds has been carried out as described in the scheme using podophyllotoxin obtained from the resin. The cytotoxicity of 4a–4p values have been illustrated in the Table 1.

TABLE 1

Cytotoxicity (in vitro) data for some representative compounds.

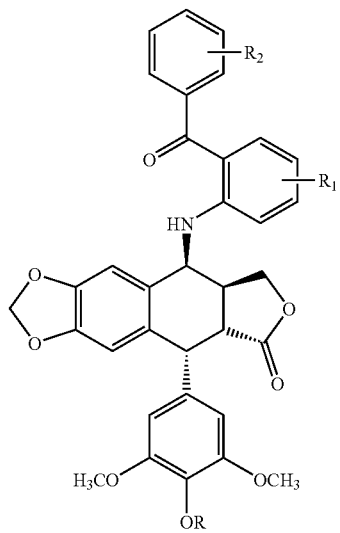

| S. No. | R | $R_1$ | $R_2$ | $GI_{50}$ μM |
|---|---|---|---|---|
| 4a | $CH_3$ | H | H | 0.04–0.5 |
| 4b | H | H | H | 15–382 |
| 4c | $CH_3$ | 2-Cl | 4-Cl | 0.059–0.876 |
| 4d | H | 2-Cl | 4-Cl | 0.1–0.24 |
| 4e | $CH_3$ | H | 4-$NO_2$ | <10 nM–0.28 |
| 4f | H | H | 4-$NO_2$ | 0.01–0.24 |
| 4g | $CH_3$ | H | 4-Cl | 0.07–1.1 |
| 4h | H | H | 4-Cl | 14–270 |
| 4i | $CH_3$ | 2-F | 4-Cl | 0.14–0.3 |
| 4j | H | 2-F | 4-Cl | 0.004–0.1 |
| 4k | $CH_3$ | H | H | 0.1–1 |
| 4l | H | H | H | 2–16 |
| 4m | $CH_3$ | H | 4-$NO_2$ | 0.01–0.2 |
| 4n | H | H | 4-$NO_2$ | 0.01–0.24 |
| 4o | $CH_3$ | H | 4-$NH_2$ | 0.04–1 |
| 4p | H | H | 4-$NH_2$ | 0.015–0.4 |

Some of the compounds of the present invention are given below:
a) 4β-1"-[2"-(Benzoyl)anilino]-4-desoxypodophyllotoxin
b) 4'-O-Demethyl-4β-1"-[2"-(benzoyl)anilino]-4-desoxypodophyllotoxin
c) 4β-1"-[2"-(2-Chlorobenzoyl)-4"-chloroanilino]-4-desoxypodophyllotoxin
d) 4'-O-1"-[2"-(2-Chlorobenzoyl)-4"-chloroanilino]-4-desoxypodophyllotoxin
e) 4β-1"-[2"-(Benzoyl)-4"-nitroanilino]-4-desoxypodophyllotoxin
f) 4'-O-Demethyl-4β-1"-[2"-(Benzoyl)]-4"-nitroanilino]-4-desoxypodophyllotoxin
g) 4β-1"-[2"-(Benzoyl)-4"-chloroanilino]-4-desoxypodophyllotoxin
h) 4'-O-Demethyl-4β-1"-[2"-(Benzoyl)]-4"-chloroanilino]-4-desoxypodophyllotoxin
i) 4β-1"-[2"-(2-Fluorobenzoyl)-4"-chloroanilino]-4-desoxypodophyllotoxin
j) 4'-O-Demethyl-4β-1"-[2"-(2-Fluorobenzoyl)-4"-chloroanilino]-4-desoxypodophylltoxin
k) 4β-1"-[3"-(Benzoyl)anilino]-4-desoxypodophyllotoxin
l) 4'-O-Demethyl-4β-1"-[3"-(benzoyl)anilino]-4-desoxypodophyllotoxin
m) 4β-1"-[2"-(Benzoyl)-2"-nitroanilino]-4-desoxypodophyllotoxin
n) 4'-O-Demethyl-4β-1"-[4"-(Benzoyl)]-2"-nitroanilino]-4-desoxypodophyllotoxin.

The following examples are given by way of illustration and should not be construed the limit and the scope of the invention.

Experimental

EXAMPLE 1

4β-1"-[2"-(Benzoyl)anilino]-4-desoxypodophyllotoxin (4a):—4β-Bromo-4-desoxypodophyllotoxin (0.1 g, 0.21 mmol) was reacted with 2-aminobenzophenone (0.045 g, 0.23 mmol) in presence of $Et_3N$ (0.032 g, 0.32 mmol) and $Bu_4N^+I^-$ (0.015 g, 0.042 mmol) in dry tetrahydrofuran at room temperature for 4 h. After completion of reaction solvent was removed in vacuo. The residue was subjected to silica gel column chromatography using chloroform-methanol (9.8:0.2) as eluent.

Yield 60%, mp 140° C.; $[\alpha]^{25}_D$ −112 (c, 0.1 $CHCl_3$) $^1H$ NMR (200 MHz, $CDCl_3$): δ 8.82 (d, 1H), 7.50 (m, 7H), 6.80 (s, 1H), 6.75 (d, 1H), 6.68 (d, 1H), 6.55 (s, 1H), 6.35 (s, 2H), 5.96 (d, 2H), 5.38 (s, 1H), 4.92 (m, 1H), 4.65 (d, 1H), 4.35 (t, 1H), 3.96 (t, 1H), 3.82 (d, 9H), 3.20 (q, 1H), 3.50 (m, 1H) MS (m/e) 593 ($M^+$, 40%), 576, 467, 397, 282, 229, 185. IR (KBr) $cm^{-1}$: 3400 (N—H), 2900 (aliphatic C—H), 1780 (lactone), 1650 (ketone), 1500, 1480, 1410, 1300, 1250 (aromatic C=C).

EXAMPLE 2

4'-O-Demethyl-4β-1"-[2"-(benzoyl)anilino]-4-desoxypodophyllotoxin (4b):—4β-Bromo-4'-O-demethyl-4-desoxypodophyllotixin (0.1 g, 0.21 mmol) was reacted with 2-aminobenzophenone (0.045 g, 0.23 mmol) in presence of $Et_3N$ (0.032 g, 0.32 mmol) and $Bu_4N^+I^-$ (0.015 g, 0.042 mmol) in dry tetrahydrofuran at room temperature for 4 h. After the completion of reaction solvent was removed in vacuo. The residue was subjected to silica gel column chromatography using chloroform-methanol (9.8:0.2) as eluent.

Yield 50% m.p 154–156° C.; $[\alpha]^{25}_D$ 111 (c, 1.1, CHCl$_3$) $^1$H NMR (200 MHz, CDCl$_3$): δ 8.85 (d, 1H), 7.50 (m, 7H), 6.80 (s, 1H), 6.75 (d, 1H), 6.68 (d, 1H), 6.55 (s, 1H), 6.35 (s, 2H), 5.96 (d, 2H), 5.38 (s, 1H), 4.92 (m, 1H), 4.65 (d, 1H), 4.35 (t, 1H), 3.96 (t, 1H), 3.82 (s, 6H), 3.20 (q, 1H), 3.05 (m, 1H) MS (m/e) 579(M$^+$, 25%), 495, 467, 397, 229, 185. IR (KBr) cm$^{-1}$: 3550 (O—H), 3400(N—H) 2900 (aliphatic C—H), 1750 (lactone), 1650 (ketone), 1500, 1480, 1410, 1300, 1250 (aromatic C═C).

EXAMPLE 3

4β-1"-[2"-(2-Chlorobenzoyl)-4"-chloroanilino]-4-desoxypodophyllotoxin (4c):—4β-bromo-4-desoxypodophyllotoxin (0.10 g 0.21 mmol) was reacted with 2-amino-2', 5'-dichlorobenzophenone (0.06 g, 0.23 mmol) in presence of Et$_3$N (0.032 g, 0.32 mmol) and Bu$_4$N$^+$I$^-$ (0.015 g 0.042 mmol) in dry tetrahydrofuran at room temperature for 5 h. After the completion of reaction solvent was removed in vacuo. The residue was subjected to silica gel column chromatography using chloroform-methanol (9.7:0.3) as eluent.

Yield 64% m.p 142–145° C.; $[\alpha]^{25}_D$ –84 (c, 0.87, CHCl$_3$) $^1$H NMR (200 MHz, CDCl$_3$): δ 9.10 (d, 1H), 7.40 (m, 5H), 7.20 (d, 1H), 6.78 (s, 1H), 6.75 (d, 1H), 6.52 (s, 1H), 6.35 (s, 2H), 5.96 (d, 2H), 4.97 (m, 1H), 4.65 (d, 1H), 4.35 (t, 1H), 3.90 (t, 1H), 3.77 (d, 9H), 3.20 (q, 1H), 3.10 (m, 1H) MS (m/e) 663 (M$^+$, 20%), 662, 661, 460, 387, 289. IR (KBr) cm$^{-1}$: 3350 (N—H), 2900 (aliphatic C—H), 1760 (lactone), 1640 (ketone), 1550, 1480, 1250 (aromatic C═C).

EXAMPLE 4

4'-O-Demethyl-4β-1"-[2"-(2-Chlorobenzoyl)-4"-chloroanilino]-4-desoxypodo-phyllotoxin (4d):—4β-Bromo-4'-O-Demethyl-4-desoxypodophyllotoxin (0.10 g 0.21 mmol) was reacted with 2-amino-2', 5'-dichlorobenzophenone (0.06 g, 0.23 mmol) in presence of Et$_3$N (0.032 g, 0.32 mmol) and Bu$_4$N$^+$I$^-$ (0.015 g 0.042 mmol) in tetrahydrofuran at room temperature for 5 h. After the completion of reaction solvent was removed in vacuo. The residue was subjected to silica gel column chromatography using chloroform-methanol (9.7:0.3) as eluent.

Yield 70% m.p 151–153° C.; $[\alpha]^{25}_D$ –91 (c, 0.93., CHCl$_3$) $^1$H NMR (200 MHz, CDCl$_3$): δ 9.10 (d, 1H), 7.40 (m, 5H), 6.77 (s, 1H), 6.70 (d, 1H), 6.30 (s, 1H), 5.96 (d, 2H), 5.40 (s, 2H), 4.90 (m, 1H), 4.65 (d, 1H), 4.30 (t, 1H), 4.10 (t, 1H), 3.80 (s, 6H), 3.20 (q, 1H), 3.10 (m, 1H). MS (m/e) 649 (M$^+$, 20%), 648, 647, 446, 383, 289. IR (KBr) cm$^{-1}$: 3320 (N—H), 2900 (aliphatic C—H), 1760 (lactone), 1650 (ketone), 1550, 1480, 1410, 1250 (aromatic C═C).

EXAMPLE 5

4β-1"-[2"-(Benzoyl)-4"-nitroanilino]-4-desocypodophyllotocin (4e):—4β-Bromo-4-desoxypodophyllotoxin (0.1 g, 0.21 mmol) was reacted with 2-amino-5-nitro-benzophenone (0.056 g, 0.23 mmol) in presence of Et$_3$N (0.032 g, 0.32 mmol) and Bu$_4$N$^+$I$^-$ (0.015 g, 0.042 mmol) in dry tetrahydrofuran at room temperature for 8 h. After completion of reaction solvent was removed in vacuo. The residue was subjected to silica gel column chromatography using chloroform-methanol (9.5:0.5) as eluent.

Yield 40%, mp 163–167° C.; $[\alpha]^{25}_D$ –85 (c, 1.2, CHCl$_3$) $^1$H NMR (200 MHz, CDCl$_3$): δ 9.50 (d, 1H), 8.57 (d, 1H), 8.32 (q, 1H), 7.60 (m, 4H), 6.75 d, 1H), 6.75 (d, 1H), 6.60 (d, 1H), 6.40 (d, 1H), 6.30 (s, 2H), 6.00 (d, 2H), 5.05 (m, 1H), 4.70 (d, 1H), 4.40 (t, 1H), 3.90 (t, 1H) 3.80 (d, 9H), 3.15 (d, 1H), 2.95 (m, 1H) MS (m/e) 638 (M$^+$, 10%), 582, 496, 439, 411, 383, 289. IR (KBr) cm$^{-1}$: 3450 (N—H), 2950 (aliphatic C—H), 1740 (lactone), 1650 (ketone), 1550, 1480, 1250 (aromatic C═C).

EXAMPLE 6

4'-O-Demethyl-4β-1"-[2"-(Benzoyl)]-4"-nitroanilino]-4-desoxypodophyllotoxin (4f):—4β-Bromo-4'-O-demethyl-4-desoxypodophyllotoxin (0.1 g, 0.21 mmol) was reacted with 2-amino-5-nitro-benzophenone (0.056 g, 0.23 mmol) in presence of Et$_3$N (0.032 g, 0.32 mmol) and Bu$_4$N$^+$I$^-$ (0.15 g, 0.042 mmol) in dry tetrahydrofuran at room temperature for 8 h. After completion of reaction solvent was removed in vacuo. The residue was subjected to silica gel column chromatography using chloroform-methanol (9.5:0.5) as eluent.

Yield 38%, mp 169–171° C.; $[\alpha]^{25}_D$ –89 (c, 1.0, CHCl$_3$) $^1$H NMR (200 MHz, CDCl$_3$): δ 9.47 (d, 1H), 8.55 (d, 1H), 8.30 (q, 1H), 7.60 (m, 4H), 6.80 (d, 1H), 6.55 (s, 1H) 6.35 (d, 1H), 6.30 (s, 2H), 6.00 (d, 2H), 5.87 (s, 1H), 5.00 (m, 1H), 4.65 (d, 1H), 4.30 (m, 2H), 3.80 (d, 6H), 3.15 (d, 1H), 2.00 (m, 1H) MS (m/e) 624(M$^+$, 15%), 568, 401, 383, 289, 229, 185. IR (KB*r*) cm$^{-1}$: 3560 (O—H), 3400 (N—H) 2900 (aliphatic C—H), 1740 (lactone), 1650 (ketone), 1500, 1480, 1250 (aromatic C═C).

EXAMPLE 7

4β-1"-[2"-(Benzoyl)-4"-chloroanilino]-4-desoxypodophyllotoxin (4g):—4β-bromo-4-desoxypodophyllotoxin (0.10 g 0.21 mmol) was reacted with 2-amino-5-chlorobenzophenone (0.053 g, 0.23 mmol) in presence of Et$_3$N (0.032 g, 0.32 mmol) and Bu$_4$N$^+$I$^-$ (0.015 g 0.042 mmol) in at room tetrahydrofuran temperature for 6 h. After the completion of reaction solvent was removed in vacuo. The residue was subjected to silica gel column chromatography using chloroform-methanol (9.7:0.3) as eluent.

Yield 56% m.p 139–142° C.; $[\alpha]^{25}_D$ –103 (c, 0.93, CHCl$_3$) $^1$H NMR (200 MHz, CDCl$_3$): δ 8.72 (d, 1H), 7.60 (m, 7H), 7.45 (q, 1H), 6.80 (s, 1H), 6.75 (d, 1H), 6.55 (s, 1H), 6.35 (s, 2H), 5.98 (d, 2H), 4.95 (m, 1H), 4.65 (d, 1H), 4.40 (t, 1H), 3.95 (t, 1H), 3.80 (d, 9H), 3.20 (q, 1H), 3.10 (m, 1H) MS (m/e) 628 (M$^+$, 20%), 627, 441, 383, 289, 229, 185 IR (KBr) cm$^{-1}$: 3350 (N—H), 2900 (aliphatic C—H), 1780 (lactone), 1660 (ketone), 1500, 1480, 1410, 1250 (aromatic C═C).

EXAMPLE 8

4'-O-Demethyl-4β-1"-[2"-(Benzoyl)]-4"-chloroanilino]-4-desoxypodophyllotoxin (4h):—4β-Bromo-4'-O-demethyl-4-desoxypodophyllotoxin (0.1 g, 0.21 mmol) was reacted with 2-amino-5-chlorobenzophenone (0.053 g, 0.23 mmol) in presence of Et$_3$N (0.032 g, 0.32 mmol) and Bu$_4$N$^+$I$^-$ (0.015 g, 0.042 mmol) in dry tetrahydrofuran at room temperature for 6 h. After completion of the reaction solvent was removed in vacuo. The residue was subjected to silica gel column chromatography using chloroform-methanol (9.7:0.3) as eluent.

Yield 50%, mp 146–149° C.; $[\alpha]^{25}_D$ –105 (c, 0.97, CHCl$_3$) $^1$H NMR (200 MHz, CDCl$_3$): δ 8.68 (d, 1H), 7.52 (m, 7H), 7.35 (q, 1H), 6.72 (s, 1H), 6.65 (d, 1H), 6.50 (s, 1H) 6.30 (s, 2H), 5.96 (d, 2H), 5.35 (s, 1H), 4.85 (m, 1H), 4.60 (d, 1H), 4.30 (t, 1H), 3.85 (s, 6H), 3.10 (q, 1H), 3.00 (m, 1H) MS (m/e) 614 (M$^+$, 10%), 613, 401, 383, 289, 229, 185 IR (KBr) cm$^{-1}$: 3500 (O—H), 3360 (N—H) 2900 (aliphatic C—H), 1750 (lactone), 1640 (ketone), 1500, 1480, 1230 (aromatic C=C).

EXAMPLE 9

4β-1"-[2"-(2-Fluorobenzoyl)-4"-chloroanilino]-4-desoxypodophyllotoxin (4i):—4β-bromo-4-desoxypodophyllotoxin (0.10 g 0.21 mmol) was reacted with 2-amino-5-chloro-2'-fluorobenzophenone (0.057 g, 0.23 mmol) in presence of Et$_3$N (0.032 g, 0.32 mmol) and Bu$_4$N$^+$I$^-$ (0.015 g 0.042 mmol) in dry tetrahydrofuran at room temperature for 5 h. After the completion of reaction solvent was removed in vacuo. The residue was subjected to silica gel column chromatography using chloroform-methanol (9.7:0.3) as eluent.

Yield 68% m.p 123–128° C.; [α]$^{25}_D$ –89 (c, 1.0, CHCl$_3$) $^1$H NMR (200 MHz, CDCl$_3$): δ 9.10 (d, 1H), 7.45 (m, 6H), 6.80 (s, 1H), 6.75 (d, 1H), 6.55 (s, 1H), 6.35 (s, 2H), 6.00 (d, 2H), 4.95. (m, 1H), 4.70 (d, 1H), 4.40 (t, 1H), 3.95 (t, 1H), 3.82 (d,9H), 3.10(m,1H) MS (m/e) 646 (M$^+$, 30%), 645, 631, 411, 397, 229, 185 IR (KBr) cm$^{-1}$: 3400 (N—H), 2950 (aliphatic C—H), 1760 (lactone), 1650 (ketone), 1500, 1480, 1300, 1250 (aromatic C=C).

EXAMPLE 10

4'-O-Demethyl-4β-1"-[2"-(2-Fluorobenzoyl)-4"-chloroanilino]-4-desoxypodo-phyllotoxin (4j):—4β-Bromo-4'-O-Demethyl-4-desoxypodophyllotoxin (0.10 g 0.21 mmol) was reacted with 2-amino-5-chloro-2-fluorobenzophenone (0.057 g, 0.23 mmol) in presence of Et$_3$N (0.032 g, 0.32 mmol) and Bu$_4$N$^+$I$^-$ (0.015 g 0.042 mmol) in dry tetrahydrofuran at room temperature for 5 h. After the completion of reaction solvent was removed in vacuo. The residue was subjected to silica gel column chromatography using chloroform-methanol (9.7:0.3) as eluent.

Yield 60% m.p 164–167° C.; [α]$^{25}_D$ –85 (c, 1.01, CHCl$_3$) $^1$H NMR (200 MHz, CDCl$_3$): δ 9.05 (d, 1H), 7.48 (m, 6H), 6.80 (s, 1H), 6.75 (d, 1H), 6.52 (s, 1H C-8), 6.35 (s, H), 6.00 (d, 2H), 5.10 (s, 1H), 4.98 (m, 1H), 4.70 (t, 1H), 4.40 (t, 1H), 3.95 (t, 1H), 3.82 (s, 6H), 3.20 (q, 1H), 3.10 (m, 1H). MS (m/e) 632 (M$^+$, 25%), 631, 401, 383, 229, 185 IR (KBr) cm$^{-1}$: 3520 (O—H), 3440(N—H), 2900 (aliphatic C—H), 1750 (lactone), 1650 (ketone), 1500, 1480, 1300, 1250 (aromatic C=C).

EXAMPLE 11

4β-1"-[3"-(Benzoyl)anilino]-4-desoxypodophyllotoxin (4k):—4β-Bromo-4-desoxypodophyllotoxin (0.1 g, 0.21 mmol) was reacted with 2-amino-4-bromobenzo-phenone (0.064 g, 0.23 mmol) in presence of Et$_3$N (0.032 g, 0.32 mmol) and Bu$_4$N$^+$I$^-$ (0.015 g, 0.042 mmol) in dry tetrahydrofuran at room temperature for 3 h. After completion of reaction solvent was removed in vacuo. The residue was subjected to silica gel column chromatography using chloroform-methanol (9.8:0.2) as eluent.

Yield 61%, mp 141–144° C.; [α]$^{25}_D$ –102 (c, 1.1, CHCl$_3$) $^1$H NMR (200 MHz, CDCl$_3$): δ 7.80 (d, 1H), 7.50 (m, 3H), 7.25 (d, 1H), 7.10 (d, 1H), 7.01(s, 1H), 6.80 (s, 1H), 6.75 (d, 1H), 6.50 (s, 1H), 6.28 (s, 2H), 5.95 (d, 2H), 5.30 (s, 1H), 4.75 (m, 1H), 4.55 (d, 1H), 4.40 (t, 1H), 4.00 (t, 1H) 3.75 (q, 9H), 3.05 (m, 2H) MS (m/e) 593 (M$^+$25%), 576, 467, 397, 229, 185. IR (KBr) cm$^{-1}$: 3400 (N—H), 2950 (aliphatic C—H), 1760 (lactone), 1650 (ketone), 1500, 1480, 1250 (aromatic C=C).

EXAMPLE 12

4'-O-Demethyl-4β-1"-[3"-(benzoyl)anilino]-4-desoxypodophyllotoxin (4l):—4β-Bromo-4'-O-demethyl-4-desoxypodophyllotixin (0.1 g, 0.21 mmol) was reacted with 3-aminobenzophenone (0.045 g, 0.23) in presence of Et$_3$N (0.032 g, 0.32 mmol) and Bu$_4$N$^+$I$^-$ (0.015 g, 0.042 mmol) in dry tetrahydrofuran at room temperature for 3 h. After the completion of reaction solvent was removed in vacuo. The residue was subjected to silica gel column chromatography using chloroform-methanol (9.8:0.2) as eluent.

Yield 63% m.p 151–154° C.; [α]$^{25}_D$ –102; (c, 1.1. CHCl$_3$) $^1$H NMR (200 MHz, CDCl$_3$): δ 7.84 (d, 2H), 7.52 (m, 3H), 7.25 (d, 1H), 7.10 (d, 1H), 7.01(s, 1H), 6.90 (s, 1H), 6.78 (d, 1H), 6.54 (s, 1H), 5.95 (d, 2H), 4.75 (m, 1H), 4.55 (d, 1H), 4.40 (t, 1H), 4.00 (t, 1H), 3.75 (d, 9H), 3.05 (m, 2H) MS (m/e) 579 (M$^+$, 25%) 382, 283, 229, 185. IR (KBr) cm$^{-1}$: 3520 (O—H), 3390 (N—H) 2900 (aliphatic C—H), 1760 (lactone), 1650 (ketone), 1500, 1480, 1250 (aromatic C=C).

EXAMPLE 13

4β-1"-[2"-(Benzoyl)-2"-nitroanilino]-4-desoxypodophyllotoxin (4m):—4β-Bromo-4-desoxypodophyllotoxin (0.1 g, 0.21 mmol) was reacted with 4-amino-3-nitro-benzophenone (0.056 g, 0.23 mmol) in presence of Et$_3$N (0.032 g, 0.32 mmol) and Bu$_4$N$^+$I$^-$ (0.015 g, 0.042 mmol) in dry tetrahydrofuran at room temperature for 8 h. After completion of reaction solvent was removed in vacuo. The residue was subjected to silica gel column chromatography using chloroform-methanol (9.4:0.6) as eluent.

Yield 42%, mp 163–167° C.; [α]$^{25}_D$ –81 (c, 0.9, CHCl$_3$) $^1$H NMR (200 MHz, CDCl$_3$): δ 8.68 (d, 1H), 8.50 (d, 1H), 8.05 (d, 1H), 7.75 (d, 2H), 7.55 (m, 3H), 6.93 (d, 1H) 6.750 (s, 1H), 6.58 (s, 1H) 6.50 (d, 1H), 6.32 (s, 2H), 6.00 (d, 2H), 5.32 (d, 1H), 5.07 (m, 1H), 4.68 (d, 1H), 4.35 (t, 1H), 3.92 (t, 1H), 3.80 (d, 9H), 3.13 (d, 1H) MS (m/e) 638 (M$^+$, 15%), 582, 524, 428, 411, 383, 289. IR (KBr) cm$^{-1}$: 3400 (N—H), 2950 (aliphatic C—H), 1760 (lactone), 1640 (ketone), 1500, 1480, 1410, 1300, 1250 (aromatic C=C).

EXAMPLE 14

4'-O-Demethyl-4β-1"-[4"-(Benzoyl)]-2"-nitroanilino]-4-desoxypodophyllotoxin (4n):—4β-Bromo-4'-O-demethyl-4-desoxypodophyllotoxin (0.1 g, 0.21 mmol) was reacted with 4-amino-3-nitrobenzophenone (0.056 g, 0.23 mmol) in presence of Et$_3$N (0.032 g, 0.32 mmol) and Bu$_4$N$^+$I$^-$ (0.015 g, 0.042 mmol) in dry tetrahydrofuran at room temperature for 8 h. After completion of reaction solvent was removed in vacuo. The residue was subjected to silica gel column chromatography using chloroform-methanol (9.6:0.4) as eluent.

Yield 34%, mp 170–175° C.; [α]$^{25}_D$ –85 (c, 1.0, CHCl$_3$) $^1$H NMR (200 MHz, CDCl$_3$): δ 8.70 (d, 1H), 8.50 (d, 1H), 8.10 (d, 1H), 7.75 (m, 3H), 6.93 (d, 1H), 6.72 (s, 1H) 6.58 (s, 1H), 6.32 (s, 2H), 6.00 (d, 2H), 5.40 (s, 1H), 5.05 (m, 1H), 4.65 (d, 1H), 4.35 (t, 2H), 3.90 (t, 1H), 3.80 (s, 6H), 3.10 (d, 2H) MS (m/e) 624 (M$^+$, 15%), 467, 401, 229, 185 IR (KBr) cm$^{-1}$: 3530 (O—H), 3450 (N—H) 2900 (aliphatic C—H), 1750 (lactone), 1650 (Ketone), 1500, 1480, 1410, 1250 (aromatic C=C).

In conclusion, the main advantages of the present inventions are that these new 4β-1"-[2"-(substituted benzoyl) anilino] podophylotoxin analogues have exhibited promising in vitro cytotoxic activity and enhanced potential as anticancer agents. Further, these compounds have been prepared 4β-bromopodophylltoxin upon reaction with the corresponding 2-aminobenzophenone in the presence of Et₃N and BU₄N⁺I⁻ at room temperature to provide the 4β-1″-[2″-(substituted benzoyl)anilino] podophylotoxin analogues in very good yields and in almost stereoselective manner.

The invention claimed is:

1. Analogs of 4β-1″-[{2″-benzoyl substituted}anilino] podophyllotoxin of compound 2

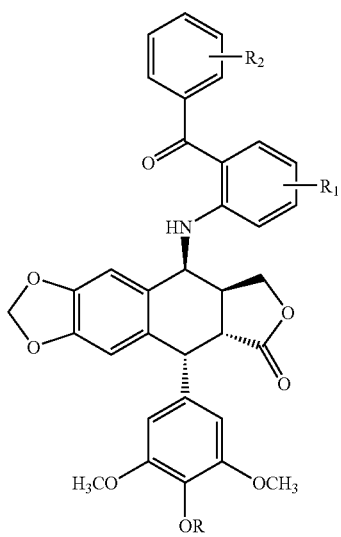

compound 2 wherein R, R₁ and R₂ independently or in combination represents
R=H or CH₃
R₁=H or halogen
R₂=H, NO₂ or halogen.

2. Analogs of 4β-1″-[{2″-benzoyl substituted}anilino] podophyllotoxin as claimed in claim 1 selected from the group consisting of:

| S. No | R | R₁ | R₂ | GI₅₀ µM |
|---|---|---|---|---|
| 4a | CH₃ | H | H | 0.04–0.5 |
| 4b | H | H | H | 15–382 |
| 4c | CH₃ | 2-Cl | 4-Cl | 0.059–0.876 |
| 4d | H | 2-Cl | 4-Cl | 0.1–0.24 |
| 4e | CH₃ | H | 4-NO₂ | <10 nM–0.28 |
| 4f | H | H | 4-NO₂ | 0.01–0.24 |
| 4g | CH₃ | H | 4-Cl | 0.07–1.1 |
| 4h | H | H | 4-Cl | 14–270 |
| 4I | CH₃ | 2-F | 4-Cl | 0.14–0.3 |
| 4j | H | 2-F | 4-Cl | 0.004–0.1 |
| 4k | CH₃ | H | H | 0.1–1 |
| 4l | H | H | H | 2–16 |
| 4m | CH₃ | H | 4-NO₂ | 0.01–0.2 |
| 4n | H | H | 4-NO₂ | 0.01–0.24 |
| 4o | CH₃ | H | 4-NH₂ | 0.04–1 |
| 4p | H | H | 4-NH₂ | 0.015–0.4 |

3. A process for the preparation of 4β-1″-[{2″-benzoyl substituted}anilino] podophyllotoxin analogs of Compound 2

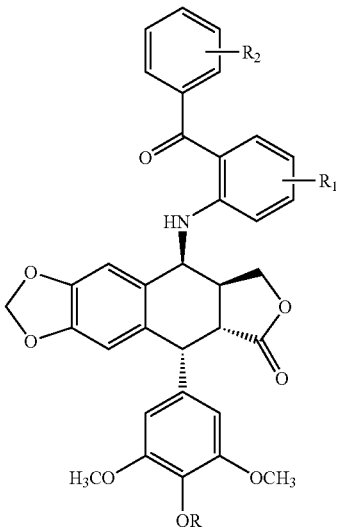

Compound 2 wherein R, R₁ and R₂ independently or in combination represents
R=H or CH₃
R₁=H or halogen
R₂=H, NO₂ or halogen
the process comprising the following steps:
a) reacting 4β-bromo-4-dioxypodophyllotoxin with substituted or unsubstituted 2-aminobenzophenone in presence of phase transfer catalyst, base in an anhydrous organic solvent medium at a temperature ranging between −10° to 40° C. for 4–16 hours,
b) removing the organic solvent from the reaction mixture of step (a) under reduced pressure to obtain a residue, and
c) purifying the residue of step (b) over silica gel column, eluting with mixture of chloroform-methanol to obtain the required 4β-1″-[{2″-benzoyl substituted}anilino] podophyllotoxin analogs.

4. A process as claimed in claim 3 wherein in step (a), the phase transfer catalyst used is selected from a group consisting of tetrabutyl ammonium chloride, tetrabutyl ammonium bromide, tetra butyl ammonium iodide or aliquat 336.

5. A process as claimed in claim 3 wherein in step (a), the substituted 2-amino benzophenone are selected from group consisting of 2-amino-2′, 5′-dichlorobenzophenone, 2-amino-5-nitrobenzophenone, 2-amino-5-chlorobenzophenone, 2-amino-5-chlorobenzophenone, 2-amino-5-chloro-2′-fluorobenzophenone, 2-amino-4′bromobenzophenone, and 4-amino-3-nitrobenzophenone.

6. A process as claimed in claim 3 wherein in step (a), the organic solvent used is selected from group consisting of dichlorormethane, chloroform, tetrahydrofuran or dioxane.

7. A process as claimed in claim 3 wherein in step (a), the base used is selected from group consisting of trimethylamine, triethylamine, sodium carbonate, potassium carbonate, cesium carbonate and barium carbonate.

8. A process as claimed in claim 3 wherein the reaction is carried out at room temperature.

9. A process as claimed in claim 3 wherein in step (a), the molar ratio of substituted or unsubstituted benzophenone and the bromocompound used is in the range of 1:1 to 2:1 and preferably 1:1.17.

10. A process as claimed in claim 3 wherein in step (a), the mole equivalent ratio of bromo compound to phase transfer catalyst is in the range of 1:0.2 to 1:0.5.

11. A method for treating cancer in a subject in need thereof comprising administering a pharmaceutically effective dosage of 4β-1"-[{2"-benzoyl substituted}anilino] podophyllotoxin analogues of general formula (2) as claimed in claim 1.

12. A method as claimed in claim 11 wherein 4β-1"-[{2"-benzoyl substituted}anilino] podophyllotoxin analogs are used singly or in combination with each other.

13. A method as claimed in claim 11 wherein the analogs of general formula (2) are administered systemically or orally.

14. A method as claimed in claim 11 wherein the subject is a mammal.

15. A method as claimed in claim 14 wherein the subject is a human.

16. A method as claimed in claim 11, wherein the compound of general formula (2) is administered to the subject in combination with pharmaceutically acceptable additives, carriers, diluent, solvent, filter, lubricant, excipient, binder or stabilizer.

17. A method as claimed in claim 11 wherein the GI 50 value of in vitro anti-cancer activity of preferred analogs is in the range of 0.001–382.

18. A process as claimed in claim 4, wherein the phase transfer catalyst is tetrabutylammonium iodide.

19. A process as claimed in claim 7, wherein the organic solvent is tetrahydrofuran.

20. A process as claimed in claim 8, wherein the base is triethylamine.

21. A process as claimed in claim 9, wherein the molar ratio is 1:1.17.

* * * * *